United States Patent [19]
DeToro

[11] Patent Number: 5,908,398
[45] Date of Patent: Jun. 1, 1999

[54] AJUSTABLE ANKLE AND FOOT ORTHOSIS BRACE

[76] Inventor: William W. DeToro, 3409 Old Winter Trail, Poland, Ohio 44514

[21] Appl. No.: 09/014,365

[22] Filed: Jan. 27, 1998

[51] Int. Cl.$^6$ ...................................................... A61F 5/00
[52] U.S. Cl. .............................................. 602/16; 602/27
[58] Field of Search ................................. 602/10–12, 16, 602/23, 27–29

[56] References Cited

U.S. PATENT DOCUMENTS

| | | |
|---|---|---|
| 4,934,355 | 6/1990 | Porcelli . |
| 5,022,390 | 6/1991 | Whiteside ................................ 602/27 |
| 5,086,760 | 2/1992 | Neumann et al. . |
| 5,088,479 | 2/1992 | DeToro . |
| 5,328,444 | 7/1994 | Whiteside ................................ 602/16 |
| 5,431,624 | 7/1995 | Saxton et al. .............................. 602/27 |
| 5,486,157 | 1/1996 | DiBenedetto . |
| 5,496,263 | 3/1996 | Fuller, II et al. . |
| 5,542,774 | 8/1996 | Hoy . |
| 5,545,127 | 8/1996 | Detoro ..................................... 602/27 |
| 5,593,383 | 1/1997 | DeToro . |
| 5,611,773 | 3/1997 | Nash et al. . |
| 5,700,237 | 12/1997 | Hess ......................................... 602/27 |

*Primary Examiner*—Linda C.M. Dvorak
*Attorney, Agent, or Firm*—Harpman & Harpman

[57] ABSTRACT

An ankle and foot orthosis brace for use in supporting and immobilization of a patient's ankle and foot. The brace is of a multiple part L-shaped configuration with a contoured leg support portion and a foot portion interconnected by an incrementally adjustable hinge assembly therebetween. A foot pad with apertured tabs extending therefrom is part of the foot portion with adjustable fabric fasteners extending from both the foot portions apertured tabs and the leg support portion secured to the brace to the patient's leg and foot.

7 Claims, 10 Drawing Sheets

AJUSTABLE ANKLE AND FOOT ORTHOSIS BRACE

BACKGROUND OF THE INVENTION

1. Technical Field

The present invention relates to leg and foot brace devices that are secured to a patient's foot and leg. Such devices are used to maintain constant pressure against the foot, sole and ankle of the patient for therapeutic purposes.

2. Description of Prior Art

Prior art devices of this type provide for a variety of leg, ankle and foot stabilization utilizing two-part brace assemblies interconnected by free hinges of an elastomeric materials as seen in U.S. Pat. No. 5,496,263 that permit the tolocural articulation to move about a single axis.

U.S. Pat. No. 5,486,157 discloses a hinge at the apex of a contoured heel portion to provide free dorsiflexion and plantar flexion with a pivot point below the hinges for inversion, eversion, pronation, and supination of the foot.

Another orthotic brace is illustrated in U.S. Pat. No. 5,086,760 which provides support to an anatomical joint that connects the lower leg with the foot that is selectively adjustable for predetermining the extent or angular range of dorsiflexion/plantar flexion and inverse/eversion of the foot. Such orthotic joints are also seen in U.S. Pat. Nos. 5,542,774 and 5,611,773.

In U.S. Pat. No. 5,542,774 a joint is illustrated having an interchangeable cam follower of shock absorbent material for more comfortable and therapeutic use.

In U.S. Pat. No. 5,611,773 multiple adjustable insert pins for an ankle pivot cap that allow for pin adjustment by movement within a contoured pivot path by corresponding registration with a dorsiflexion limiting aperture or plantar flexion limiting apertures.

A foot brace can be seen in U.S. Pat. No. 4,934,355 having a heel cup flexible connector to a leg engagement portion. The flexible connection is formed by an elastomeric block therebetween.

Applicant's own prior art patents U.S. Pat. Nos. 5,088,479 and 5,593,383 disclose orthotic devices which are characterized by an adjustable foot portion interconnected to a leg portion by a semi-flexible heel member.

U.S. Pat. No. 5,593,383 introduces a foot pad with a securing apparatus to enhance and simplify usefulness.

U.S. Pat. No. 5,088,479 discloses a basic ankle and foot orthosis device having adjustable length and height for the leg and foot portion respectively.

OBJECTS AND ADVANTAGES

Accordingly, it is an object of the present invention to provide a securing apparatus and method that provides for the static accommodation of a patient's particular range of dorsiflexion and plantar flexion motion or static position. Other objects of the present invention is to provide a securing apparatus that is conveniently adjustable by use of a composite hinge assembly that provides for limited degrees of plantar flexion and dorsiflexion in the sagital plane. The hinge assembly can be locked in a specific position defining a given angular relationship between the leg portion and the foot portion while maintaining space between the heel and bedding that is advisable for patients with posterial heel disorders.

SUMMARY OF THE INVENTION

An adjustable orthotic foot brace having a leg portion, foot portion and an incrementally adjustable heel portion communicating therebetween. The incrementally adjustable heel assembly between the foot and leg portions provide for adjustable angular inclination therebetween. Fabric foot and leg engagement straps are used to attach the leg and foot portion to the patient's foot and ankle. This invention provides for a securing apparatus that allows for limited plantar flexion and dorsiflexion of the foot portion of the sagital plane by the hinge assembly that can be locked at any point within the sagital plane range of movement. This invention further provides for an applied method for incorporation of the invention into a custom fabricated adjustable orthotic foot brace utilizing multiple fabrication steps.

DETAILED DESCRIPTION OF THE PREFERRED EMBODIMENT

Figure 1:
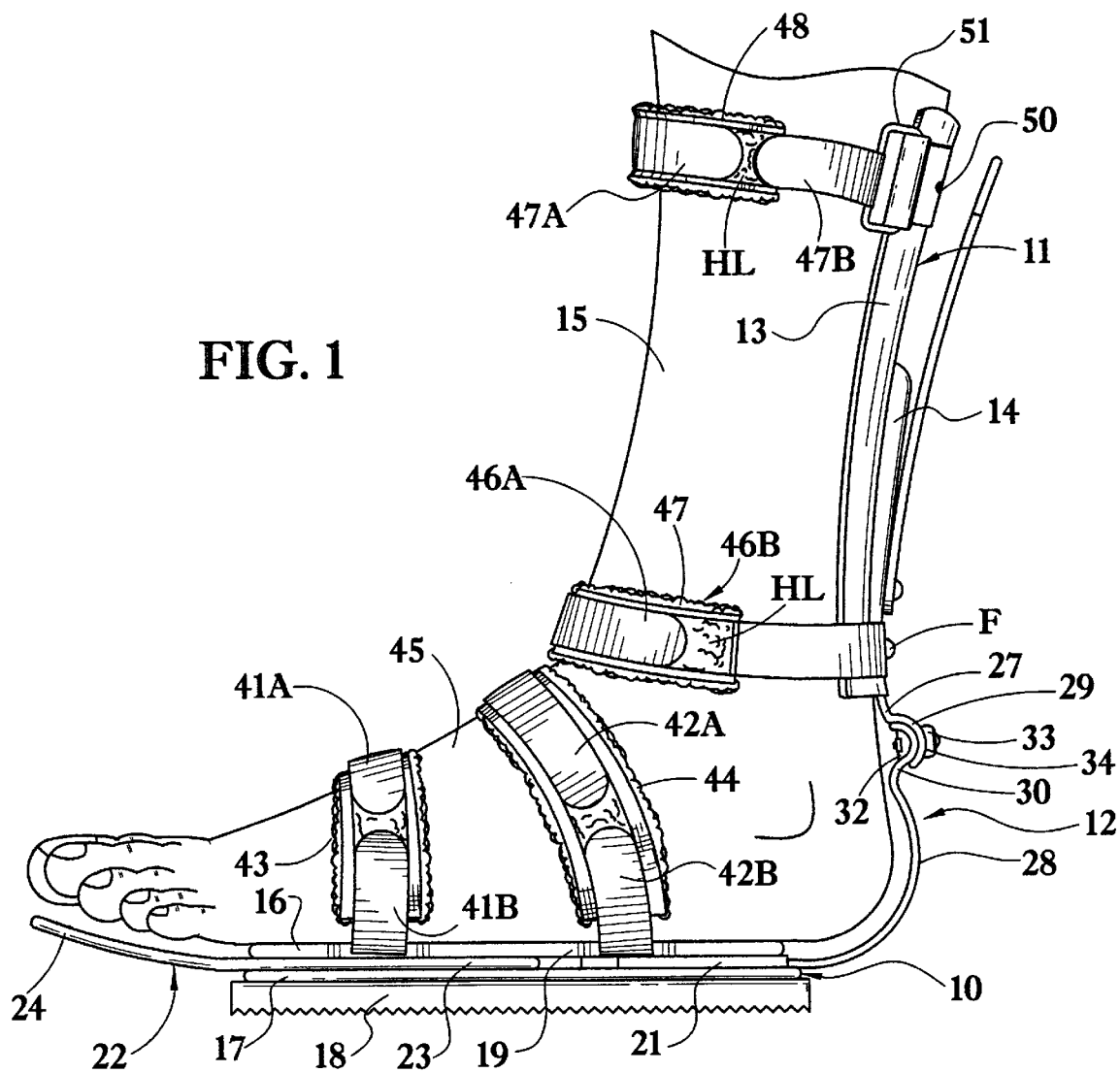
FIG. 1 is a side elevational view of the adjustable orthotic brace positioned on a patient.
Figure 2:
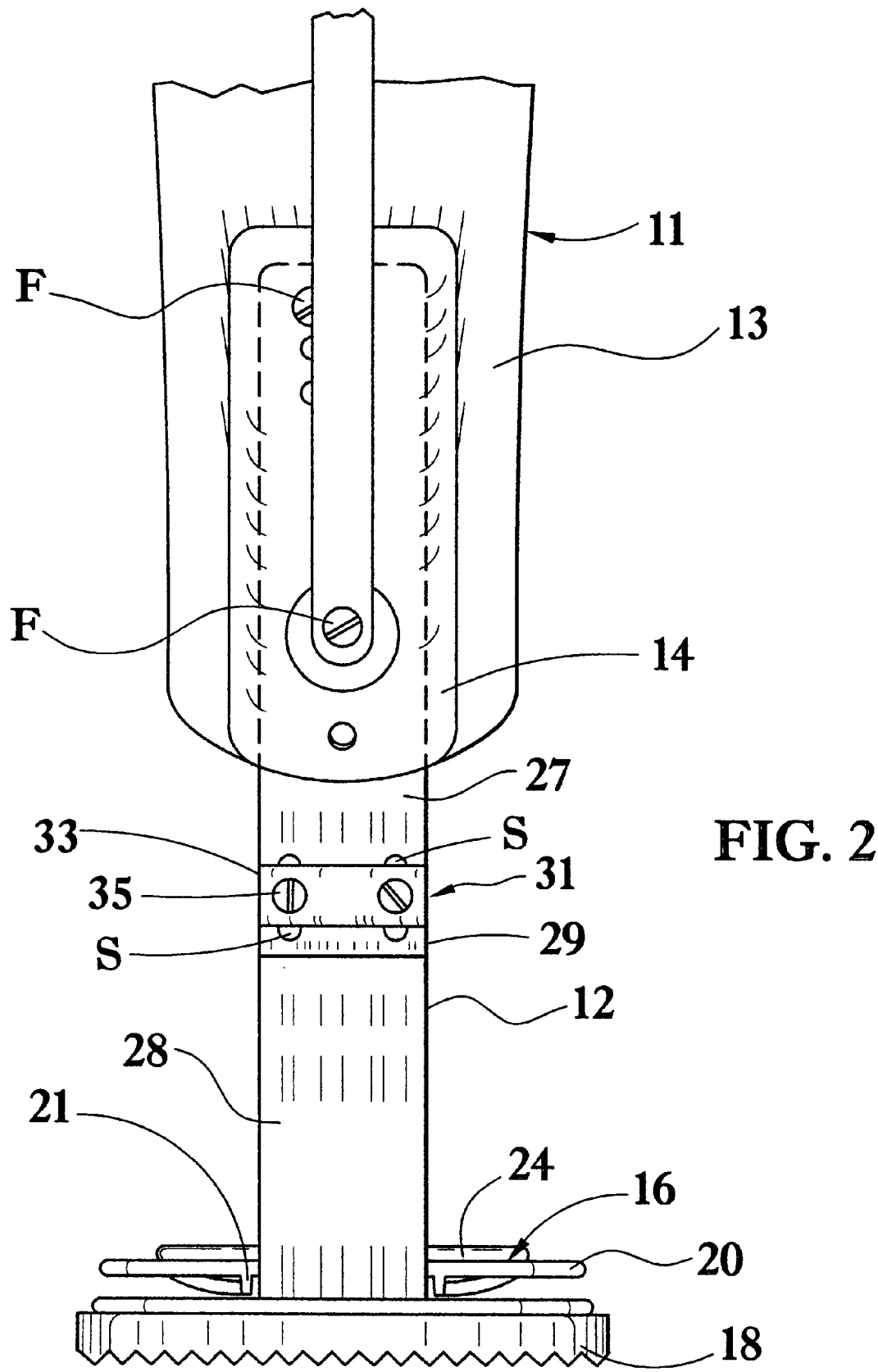
FIG. 2 is an end plan view of the leg, foot and heel portion with the incrementally adjustable hinge assembly within the heel portion.

Referring to FIGS. 1, 2, 3 and 4 of the drawings, the adjustable orthotic brace can be seen comprising a foot portion 10, a leg portion 11 and an interconnecting heel portion 12 extending therebetween. The leg portion 11 has an enlarged transversely contoured leg support 13 having a recessed channel 14 formed inwardly of one end thereof. In practice the leg and foot portions are made of synthetic plastic resin so that they can be molded or pre-formed to the desired contours required for engagement with a patent's leg 15 as best seen in FIG. 1 of the drawings.

Figure 3:
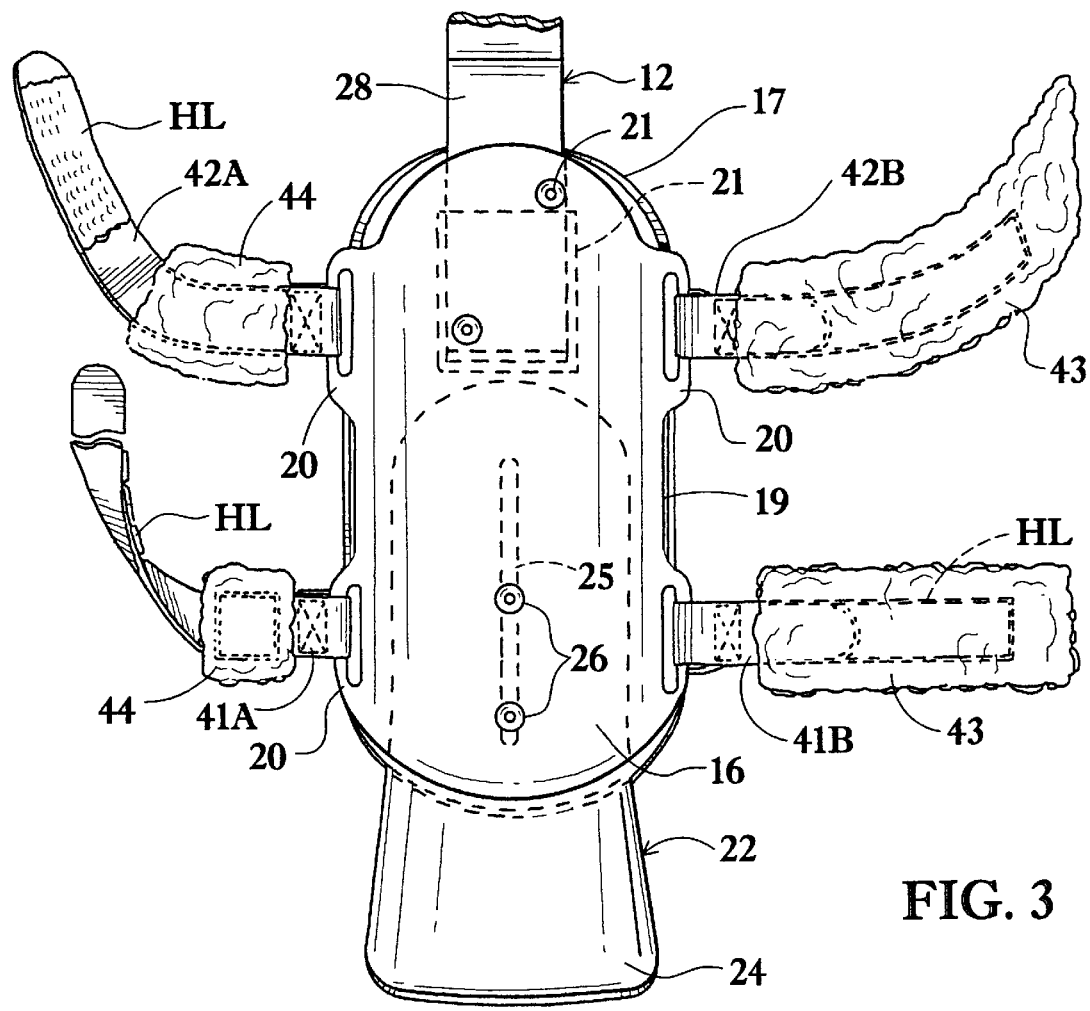
FIG. 3 is a top plan view of the foot portion with the foot pad in the securing apparatus.

The foot portion 10 has a foot pad 16 connected to a generally rectangular attachment base 17. The attachment base 17 having a resilient walking pad 18 secured thereto. The foot pad 16 is also of a generally rectangular configuration with an area of reduced transverse dimension at 19 defining pairs of longitudinally spaced aperture tabs 20, as best seen in FIG. 3 of the drawings. A mounting pocket 21 extends inwardly from the bottom of the foot pad 16 for engagement of the interconnecting heel portion 12 between the foot pad 16 and the abutting attachment base 17.

Figure 4:
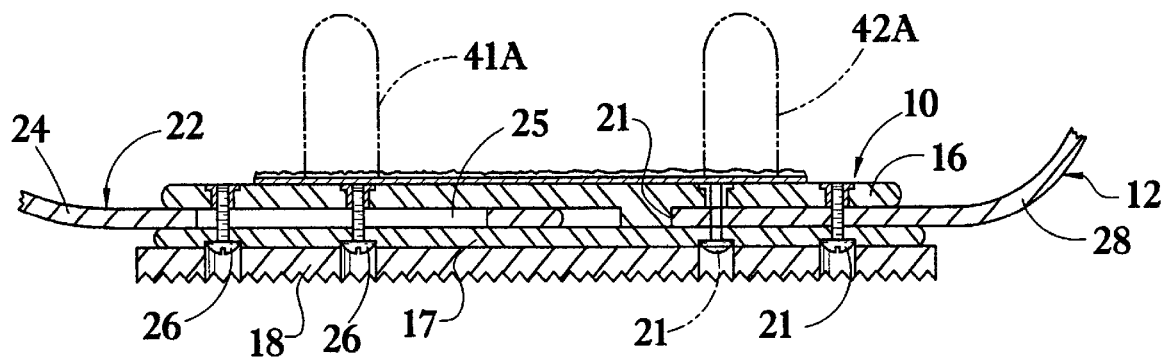
FIG. 4 is a side elevational view of the foot engagement enclosure in the securing apparatus shown in FIG. 3.

Referring now to FIGS. 3 and 4 of the drawings, a toe extension member 22 can be seen and is adjustably secured to the foot pad 16 opposite said mounting pocket 21. The toe extension member 22 has a flat base area 23 with an upturned angular offset end portion 24. The toe extension 22 is registerably attached between the foot pad 16 and the attachment base 17 by a mounting slot 25 aligned for registration with adjustable fasteners 26 extending from said foot pad 16 through the attachment base 17 allowing for lengthening of the overall foot portion 10.

The interconnecting heel portion 12 comprises an upper leg element 27 and a lower foot element 28, both comprised of a resilient metal alloy or other suitable material. The upper leg element 27 is secured within the recess channel 14 in the leg support 13 by multiple fasteners F and has an articulated contoured free end at 29. The foot element 28 extends from and is secured within the mounting pocket 21 of the foot pad 16 by pairs of fasteners F that interengage therethrough in registration with selective fixed apertures in the mounting pocket 21. The foot element 28 has an articulated curved free end at 30. The articulated curved free ends 29 and 30 of the respective leg and foot elements each have spaced parallel adjustment slots S therein that overlie one another in aligned registration as best seen in FIG. 5 of the drawings.

Referring now to FIGS. 1, 2, 5 and 6 of the drawings, it will be seen that a hinge assembly 31 is formed by the overlapping arcuate ends 29 and 30 with a hinge block 32 registerable within the arcuate free end 30 of the foot element 28 and correspondingly a compression cap fitting 33 with a curved interengagement surface 34 is positioned over the aligned slots S in the articulated free end 29 of the leg element 27 in oppositely disposed aligned relation to the hinge block 32. The hinge block 32 and compression cap fitting 33 are registerably secured together by a pair of threaded fasteners 35 extending through aligned apertures A therein and the corresponding slots S of the respective leg and foot elements 27 and 28 as hereinbefore described.

Figure 5:
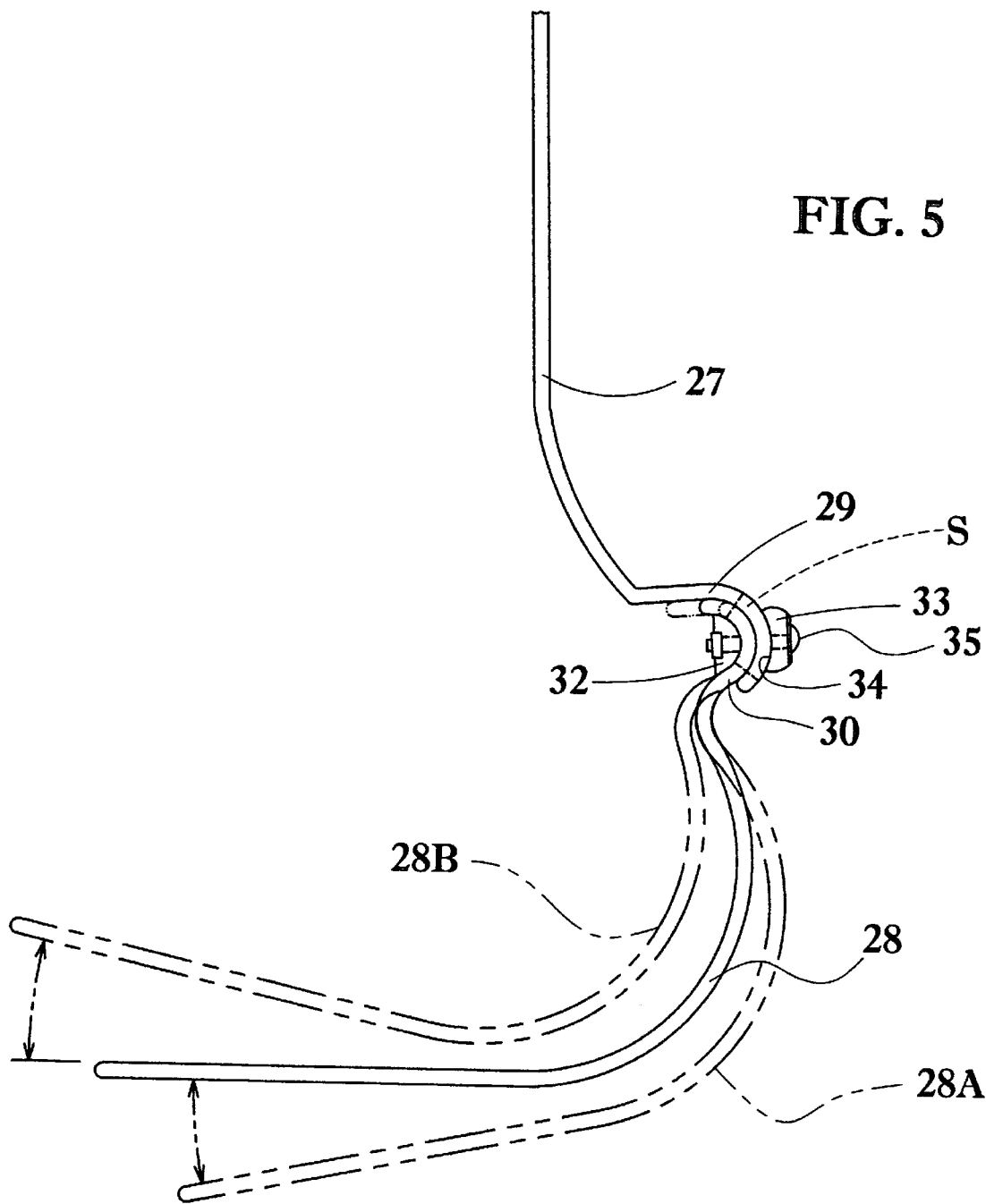
FIG. 5 is a side elevational view of the hinge and support element of the invention.
Figure 6:
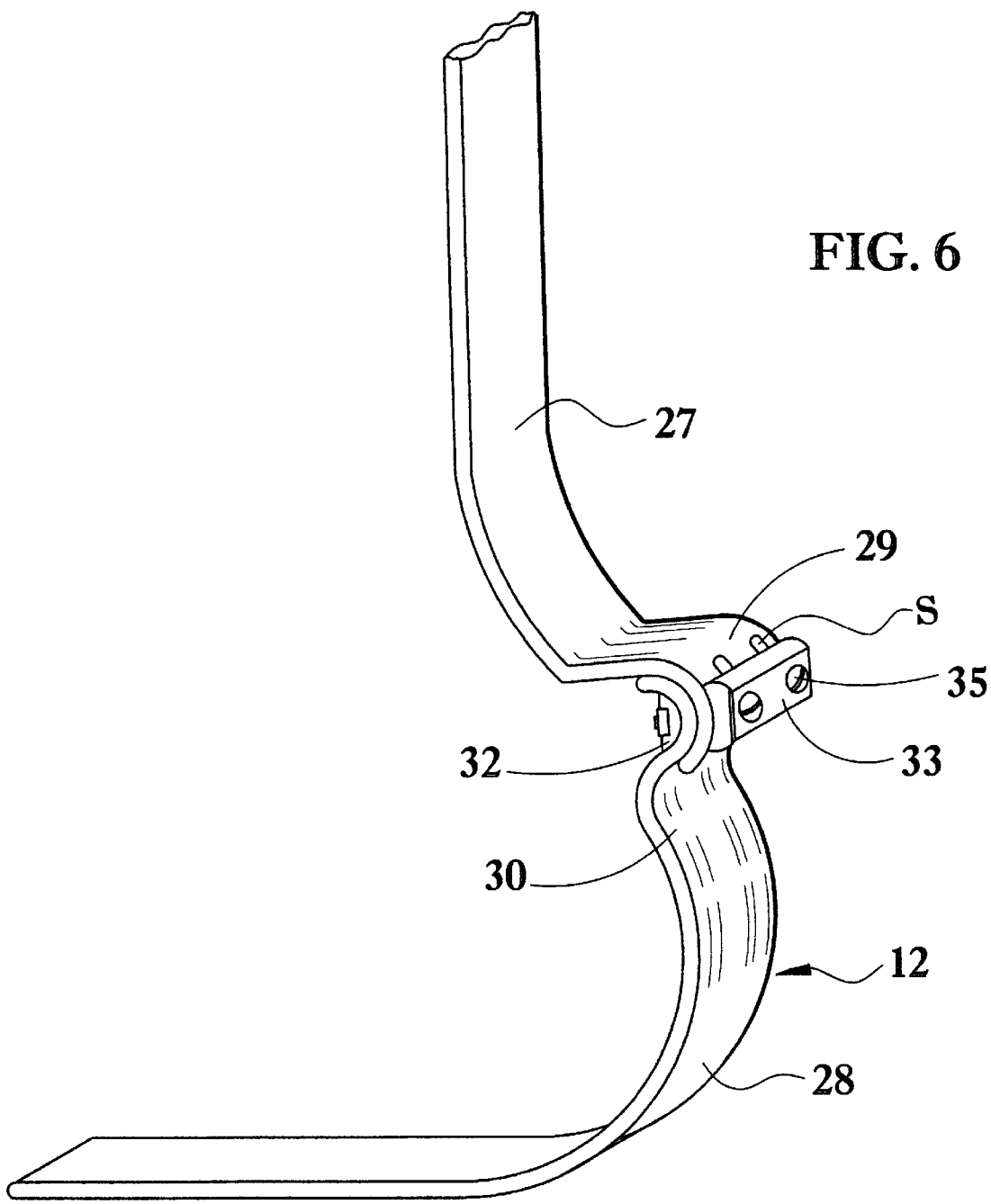
FIG. 6 is an enlarged perspective view of the hinge and support element as seen in FIG. 5.

Referring specifically to FIG. 5 of the drawings, the hinge assembly 31 can be seen allowing an effective range of motion of the foot element 28 in relation to the leg element 27 delineated by broken lines at 28A and 28B. It will be evident that the relative range of movement illustrated in broken lines of the foot element 28 is determined by the overlying aligned registration of the respective elongated slots and fasteners 35 therethrough in each of the hereinbefore described leg and foot elements 27 and 28 respectively as will be evident and well understood by those skilled in the art. It will also be seen that adjustable range of the movement of the foot element 28 illustrated in broken lines 28A is limited by the interengagement of the arcuate free end at 29 with the aforementioned registering arcuate free end 30 of the foot element 28.

Referring now to FIGS. 1 and 3 of the drawings, it will be seen that a foot engagement enclosure area is illustrated comprising the foot pad 16 and pairs of foot fastening straps 41A & 41B and 42A & 42B extending from and secured to the respective aperture tabs 20. Each of the strap pairs 41A & 41B and 42A & 42B are releasably secured to one another by hook and loop material HL on the respective strap pair ends extending inwardly therefrom. Each of the strap pairs 41 and 42 are padded at 43 and 44 respectively so as to be engageable in overlapping relation to one another about a patient's foot 45. A pair of support padded straps 46A & 46B and 47A & 47B can be seen extending from the leg support 13. The leg support strap 46A has a padded portion 47 and is secured to the leg support 13 by a fastener F. The straps 46A & 46B are adjustably secured to one another by hook and loop material HL on their respective ends. The leg support straps 47A and 47B also have padded portion at 48 and hook and loop material HL on their respective ends.

The strap pad portions 47A and 47B are removably secured to the leg support 13 by respective attachment fasteners 50 and adjustably bracket assemblies 51.

Figure 7:
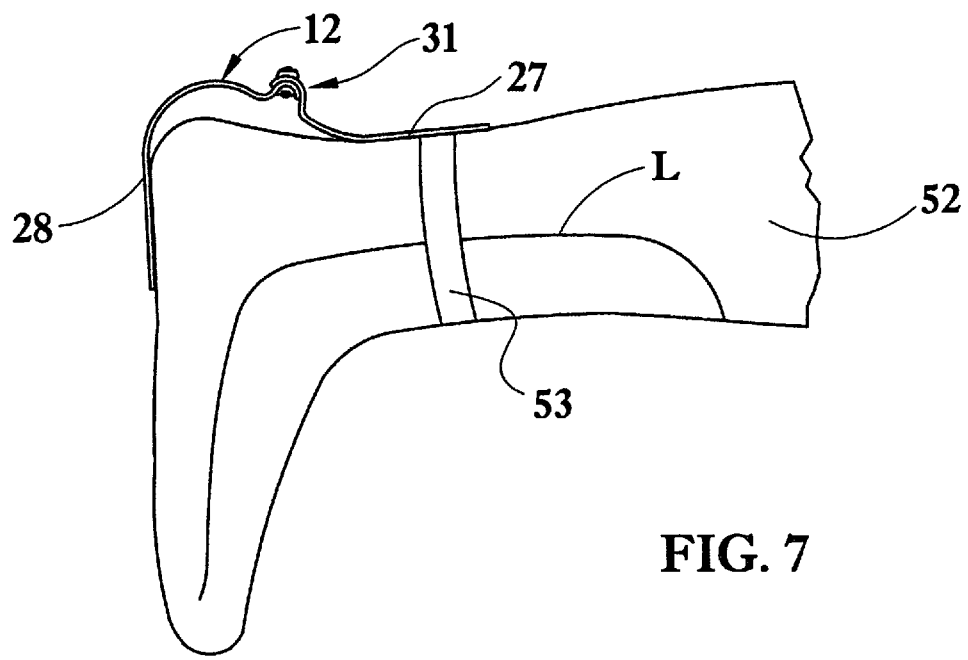
FIG. 7 is a side elevational view of the foot and leg cast formed with the hinge assembly of the invention positioned temporarily thereon.
Figure 8:
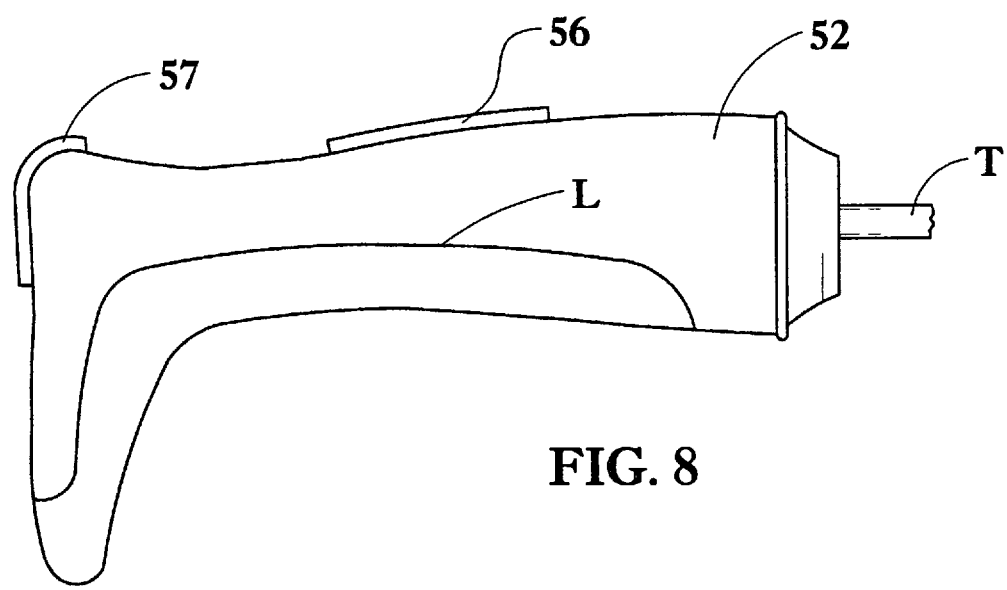
FIG. 8 is a side elevational view of the foot and leg cast with mounting block spacers positioned thereon.

Referring now to FIGS. 5 and 7–11 of the drawings, an alternate method form of the invention can be seen wherein multiple fabrication steps take place beginning with a 3-D cast 52 of the patient's leg and foot 45. The cast 52 is formed by making a negative mold of the leg as is well understood by those skilled in the art and accordingly does not require any additional explanation thereof. The cast 52 is positioned on a support and preparation tool T securing the cast 52 in an elevated accessible position. A custom orthotic 54, best seen in FIG. 12 of the drawings is to be formed by vacuum forming process that begins with the preparation of the cast 52. Initially, clearance areas needed are built up on the cast 52 to accommodate boney protuberances of the patient's foot. The cast 52 is then sanded and smoothed to provide a finished surface. Lay-out lines L for the propose custom orthotic 54 are then added. The hinge assembly 31 of the invention is typically positioned on the cast 52 by temporary straps 53 as best seen in FIG. 7 of the drawings to determine the attachment points therefore. Spacers 56 and 57 are then secured to the cast 52 at the attachment points for the formation of the actual attachment pockets P for the positioning and securing of the hinge assembly 31 within the custom orthotic 54 as seen in FIG. 8 of the drawings.

Figure 9:
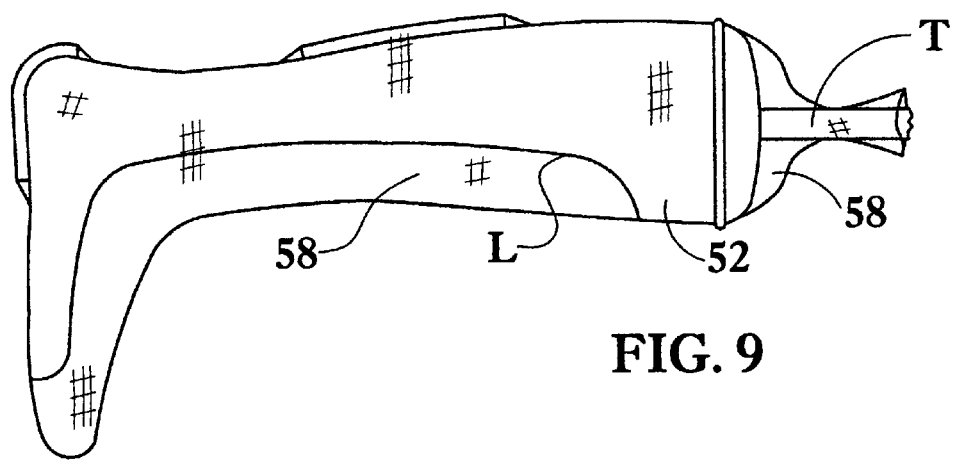
FIG. 9 is a side elevational view of the foot and leg cast with a modified release stocking thereon.
Figure 10:
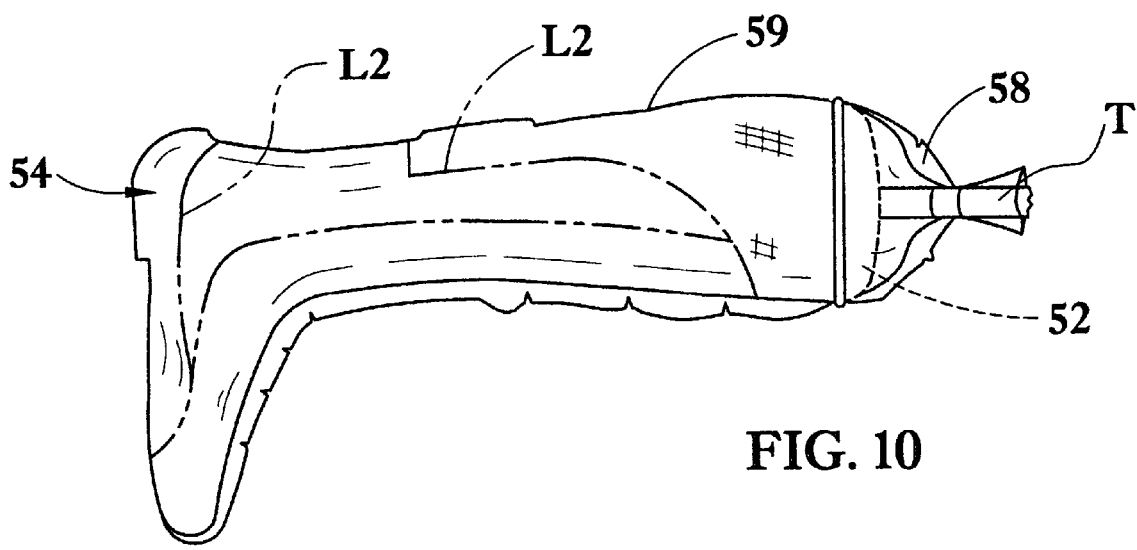
FIG. 10 is a side elevational view of the foot and leg cast with a vacuum formed heated synthetic resin sheet positioned thereabout.

Referring now to FIG. 9 of the drawings, a release stocking 58 is pulled over the cast 52 and secured to the support tool T. In the vacuum forming process, as is well know to those skilled in the art, a sheet of synthetic resin material 59 (polypropylene) is heated to soften and then applied over and around the prepared cast 52 on top of the release stocking 58. A vacuum is then applied over the surface of the cast 52 via the tool T drawing the synthetic resin sheet 59 tightly about the cast 52 as illustrated in FIG. 10 of the drawings.

Figure 11:
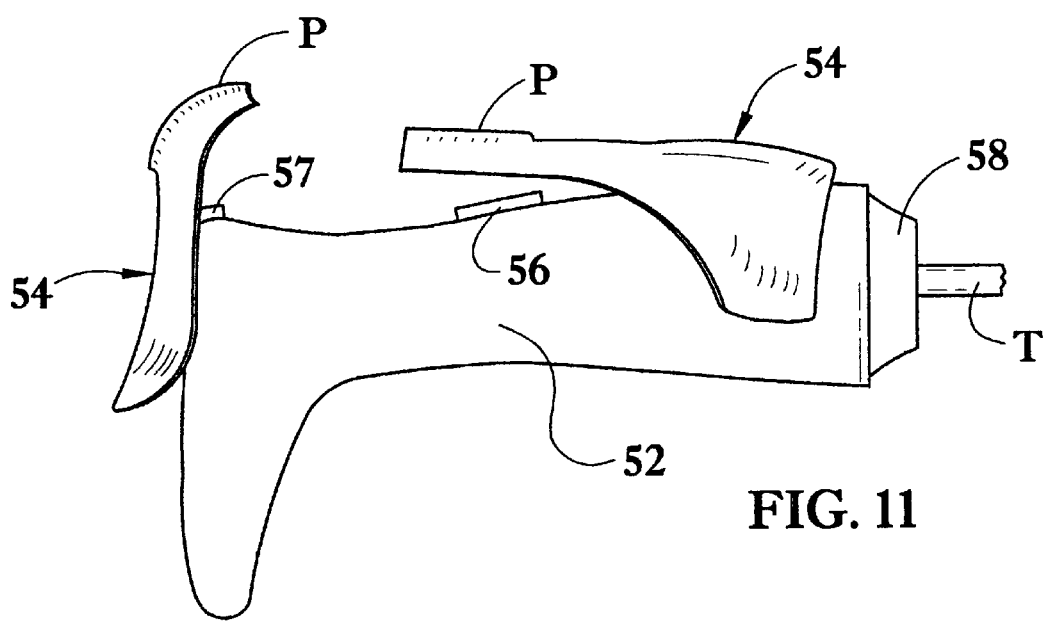
FIG. 11 is a side elevational view of the foot and leg cast illustrating the cutting and removal of the custom foot and leg support portions.
Figure 12:
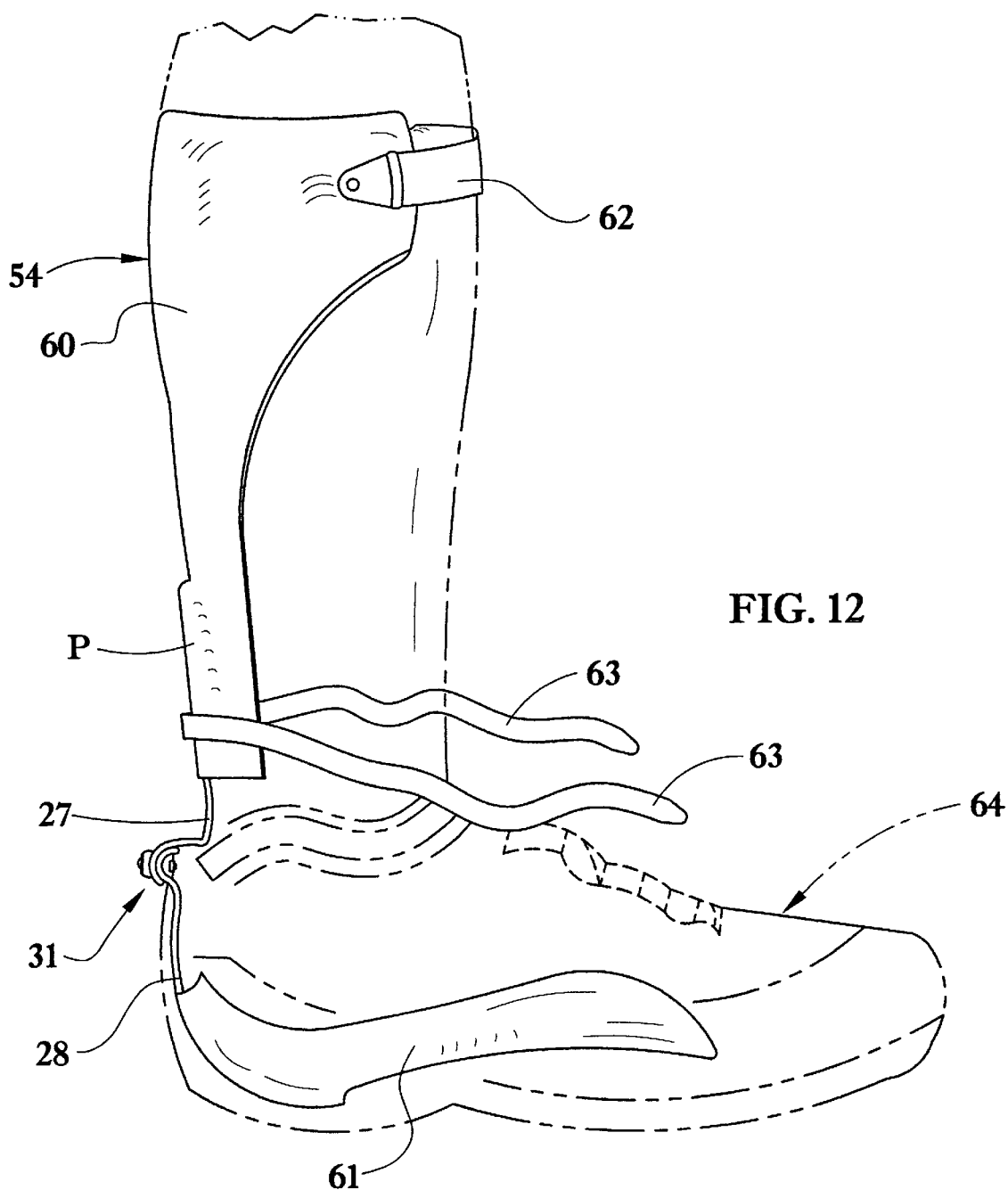
FIG. 12 is a side elevational view of an assembled custom orthotic foot brace utilizing the adjustable interconnecting resilient hinge assembly of the invention.

Referring now to FIG. 11 of the drawings, the synthetic resin sheet 59 is then cut along contoured guidelines L2 placed on the mold surface S defining the custom orthotic 54 into a custom leg portion 60 and a custom foot portion 61 with the hereinbefore described attached pockets. The hinge assembly 31 is then attached by inserting same into the respective pockets with fasteners, not shown, joining the custom leg and foot portions 60 and 61 at the hereinbefore described mounting attachment pockets formed in the vacuum forming process. Finally, attachment strap pairs 62 and 63 are secured to the custom orthotic leg portion 60 completing the assembly as seen in FIG. 12 of the drawings. Such custom orthotics 54 are typically fitting within a modified shoe 64, shown in broken lines of FIG. 12 of the drawings, with the hereinbefore described strap pairs 62 and 63 holding the custom orthotics 54 onto the patient.

Figure 13:
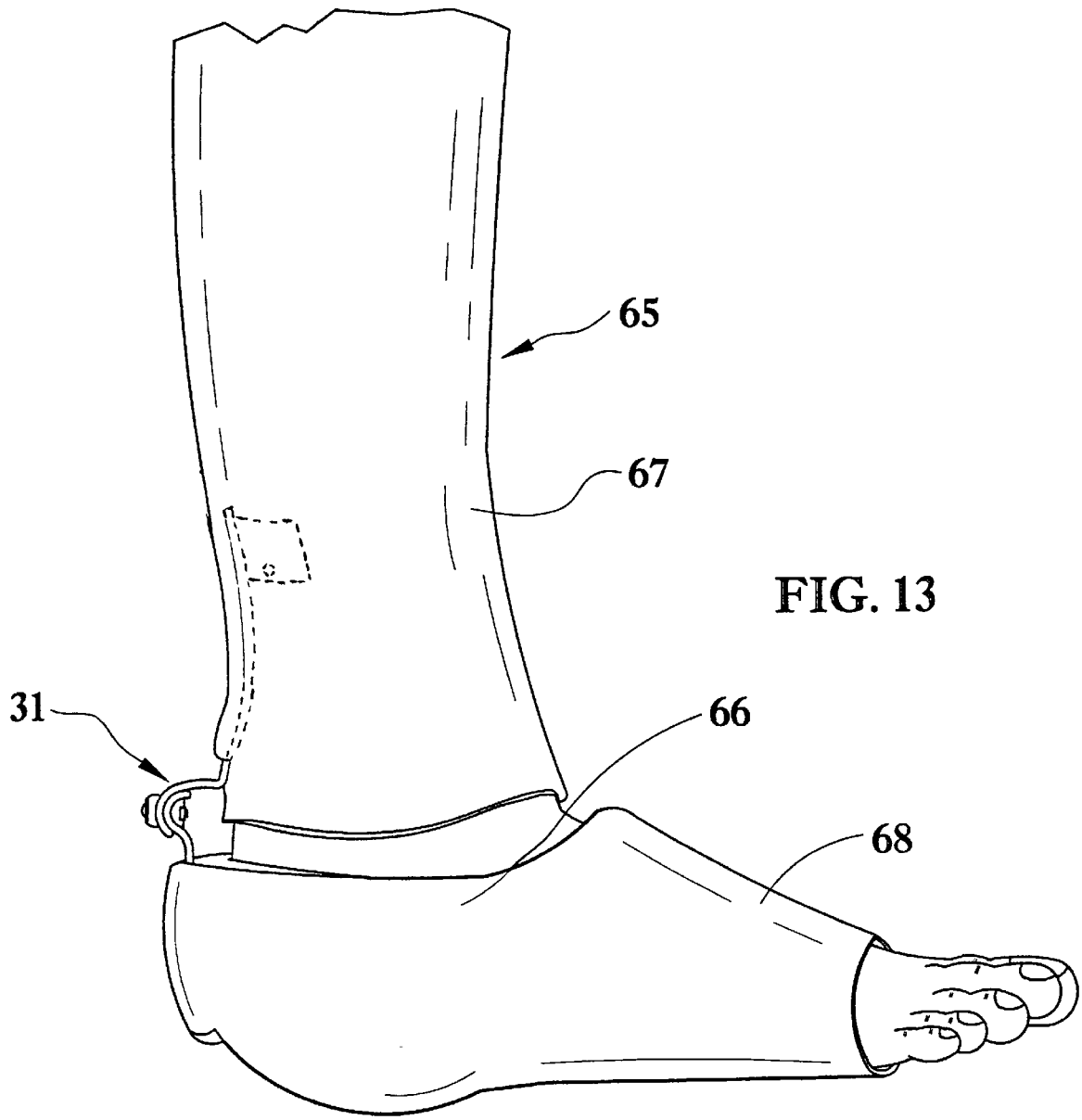
FIG. 13 is a side elevational view of an alternate form of the invention applied to a bone cast.

It will also be evident that the hinge assembly 31 of the invention can be used in other therapeutic treatment situations, such as with a typical leg cast for the treatment of broken bones as seen in FIG. 13 of the drawings. A custom bone cast 65 for the immobilization of a patient's leg 66 allowing the healing of broken bones can be formed by use of the hinge assembly 31. In this example chosen for illustration the custom bone cast 65 is formed about and on the patient's leg 66 after the bone has been set. The bone cast 65 is typically formed by building up multiple layers of fabric material saturated with a hardening medium, such as plaster of paris. As the bone cast 65 is formed, the hinge assembly 31 of the invention is incorporated so as to provide an adjustable relationship between an upper leg bone cast portion 67 and a lower foot bone cast portion 68. The hinge assembly 31 is modified with the addition of transversely extending cast tabs T, shown in broken lines extending from the upper portion 27 (for illustration purposes only) that provide additional structural stabilization of the hinge assembly 31 during the cast incorporation process. Additional tabs, not shown, can also extend from the lower foot element 28 at longitudinal angles to help with the incorporation process of the lower cast portion 66 of the bone cast 65 as will applicable and familiar with those skilled in the art of cast formation in which a saturated fabric material can be interwoven and overlapped over the tabs which again helps the stabilization of the hinge assembly 31 within the bone cast 65 as will be evident to those skilled in the art. This application of the hinge assembly 31 of the invention addresses the failures of typical bone casts of the prior art at the flexation portion between the leg and bone cast portions 67 and 68 respectively which are common. Additionally, the hinge assembly 31 will allow for incremental adjustment of the bone cast deflection as is required by the treatment protocol which heretofore could only be achieved by recasting the patient's leg or refitting with a less viable brace configuration, as will be well known and understood by those skilled in the art.

It will thus be seen that a new and novel articulated ankle and foot orthosis brace and method has been illustrated and described and it will be apparent to those skilled in the art that various changes and modifications may be made thereto without departing from the spirit of the invention.

Therefore I claim:

1. An adjustable leg and foot brace for use on a patient, said brace having a foot portion and a leg portion interconnected by an adjustable heel portion positionable substantially behind the patient's heel, said heel portion comprising an upper leg element and a lower foot element, an articulated contoured slotted end portion of said upper leg element overlapping a corresponding articulated contoured slotted end portion of said lower foot element forming a hinge assembly to allow dorsi-flexion and plantar-flexion of the patient's foot, mechanism for aligning and locking said hinge assembly fixing the angle between the foot and leg of the patient, securing said upper leg element to said leg portion securing said lower foot element of said heel portion to said foot portion.

2. The adjustable leg and foot brace set forth in claim 1, wherein said mechanism for aligning and locking said hinge assembly comprises an apertured hinge block and apertured compression cap, the apertured compression cap being in aligned relationship with said apertured hinge block, and slots of the overlapping end portions of said hinge assembly registerably aligned with the apertures of the hinge block and compression cap and a fastener extending through said apertures of said hinge block and compression cap and through said slots in each of said overlapping end portions.

3. The adjustable leg and foot brace set forth in claim 2, wherein said upper leg element and lower foot element are substantially flat and comprised of metal.

4. The adjustable leg and foot brace set forth in claim 2, wherein the overlapping end portions of said upper leg and lower foot elements forming said hinge assembly have substantially a C-shape.

5. The adjustable leg and foot brace set forth in claim 3, wherein said upper leg element is attached to said leg portion at a recessed channel in said leg portion, the recessed channel having an aperture and a fastener extend through said aperture and said upper leg element.

6. The adjustable leg and foot brace set forth in claim 3, wherein said lower foot element of said heel portion is attached to said foot engagement portion at a mounting pocket formed between a foot pad and base.

7. The adjustable leg and foot brace set forth in claim 4, wherein said hinge block is engageable against the end portion of said lower foot element and said compression cap is engageable over the end portion of said upper leg element.

* * * * *